(12) United States Patent
Zim et al.

(10) Patent No.: US 8,563,784 B2
(45) Date of Patent: Oct. 22, 2013

(54) CATALYTIC METHOD OF MANUFACTURE OF COMPOUNDS OF THE DIOL TYPE

(75) Inventors: Danilo Zim, Campinas (BR); Philippe Marion, Vernaison (FR)

(73) Assignee: Rhodia Poliamida e Especialidades Ltda, Sao Paulo (BR)

( * ) Notice: Subject to any disclaimer, the term of this patent is extended or adjusted under 35 U.S.C. 154(b) by 159 days.

(21) Appl. No.: 13/140,089

(22) PCT Filed: Dec. 15, 2009

(86) PCT No.: PCT/IB2009/007760
§ 371 (c)(1),
(2), (4) Date: Sep. 8, 2011

(87) PCT Pub. No.: WO2011/077176
PCT Pub. Date: Jun. 30, 2011

(65) Prior Publication Data
US 2011/0313204 A1     Dec. 22, 2011

(30) Foreign Application Priority Data

Dec. 16, 2008 (FR) ........................ 08 58651

(51) Int. Cl.
*C07C 29/145* (2006.01)
*C07C 29/141* (2006.01)
(52) U.S. Cl.
USPC .......................................... 568/862; 568/864
(58) Field of Classification Search
None
See application file for complete search history.

(56) References Cited

U.S. PATENT DOCUMENTS 6,969,780 B1 * 11/2005 Dubner et al. ................ 568/862

FOREIGN PATENT DOCUMENTS

JP        9-20703 A     1/1997

OTHER PUBLICATIONS

Kandegedara et al., "Noncomplexing Tertiary Amines as "Better" Buffers Covering the Range of pH 3-11. Temperature Dependence of Their Acid Dissociation Constants," Analytical Chemistry, Aug. 1, 1999, pp. 3140-3144, vol. 71, No. 15.
Mozingo, "Catalyst, Raney Nickel, W-2," Organic Syntheses, 1941, p. 15, vol. 21.
International Search Report issued on Mar. 29, 2010, by the European Patent Office as the International Searching Authority in International Patent Application No. PCT/IB2009/007760.
Written Opinion of the International Searching Authority (Form PCT/ISA/237) issued on Oct. 4, 2011, in International Patent Application No. PCT/IB2009/007760.

* cited by examiner

*Primary Examiner* — Brian J Davis
(74) *Attorney, Agent, or Firm* — Dentons US LLP

(57) ABSTRACT

The invention relates to a catalytic method for the industrial production of a diol compound, such as 2-methyl-2-4-pentanediol, also called 2,4-hexylene glycol (HGL), from a β-hydroxy carbonyl compound, Formula (I), in particular diacetone alcohol (DAA).

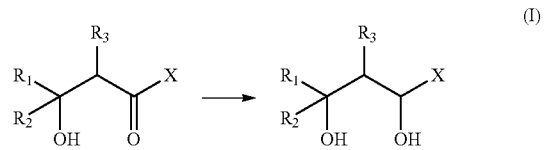

15 Claims, No Drawings

CATALYTIC METHOD OF MANUFACTURE OF COMPOUNDS OF THE DIOL TYPE

CROSS-REFERENCE TO EARLIER APPLICATIONS

This application is the United States national phase of PCT/IB2009/007760, filed Dec. 15, 2009, and designating the United States (published in the French language on Jun. 30, 2011 as WO 2011/077176 A1; the title and abstract were also published in French), which claims foreign priority under 35 U.S.C. §119 of FR 0858651, filed Dec. 16, 2008, each hereby expressly incorporated by reference in its entirety and each assigned to the assignee hereof.

The present invention relates to a catalytic method for the industrial-scale production of a compound of the diol type, such as 2-methylpentane-2-4-diol, also called 2,4-hexylene glycol, or HGL, from a β hydroxy carbonylated compound, notably diacetone-alcohol, or DAA.

PRIOR ART

HGL is prepared industrially by catalytic hydrogenation of DAA, and Raney nickel is the catalyst most used, generally in considerable proportions, notably 5-20 wt. % relative to the weight of the DAA to be hydrogenated.

The operating conditions of the hydrogenation reaction of DAA to HGL in the presence of Raney nickel catalyst cause recognized technical and economic problems, which have still not been overcome. In fact, in the conditions of the reaction, DAA can decompose by back-aldolization, thus leading to synthesis of acetone and then of isopropanol by hydrogenation. In acid conditions, DAA can also form hexenol, which is then hydrogenated to hexanol. Moreover, these acid conditions tend to deactivate or even partially dissolve the catalyst of the reaction.

Moreover, it appears that the Raney nickel must generally be washed, notably with distilled or demineralized water, for several days, before it is used in the hydrogenation reaction, so as to lower its basicity, in order to increase the selectivity of the reaction. This step is long and restricting and it would be highly desirable to omit it, for the economic and industrial interest of this reaction.

More generally, there was a need to develop an industrial process for hydrogenating β hydroxy carbonylated compounds possessing an alcohol function on the β carbon of the carbonyl function, notably an aldehyde function, obtained by reactions of aldolization, while avoiding back-aldolization of these compounds during the catalytic hydrogenation reaction.

INVENTION

The applicant has found a completely unexpected way of avoiding the drawbacks mentioned above while obtaining excellent selectivity of the hydrogenation reaction on the β hydroxy carbonylated compounds, moreover without needing a long step of catalyst washing beforehand.

The present invention thus relates firstly to a method of preparing a compound of formula (IV) by a reaction of catalytic hydrogenation of a compound of formula (III), said compound of formula (III) being obtained by a reaction of base catalysed aldolization, characterized in that said hydrogenation reaction is catalysed by a Raney catalyst that has been pretreated with at least one buffer compound enabling said hydrogenation reaction to be maintained at a pH between 6 and 8 inclusive;

the compounds of formula (III) and (IV) are as follows:

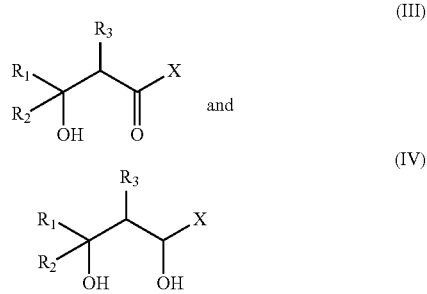

in which:
R₁ is a radical with from 1 to 10 carbon atoms,
R₂ is a hydrogen atom or a radical with from 1 to 10 carbon atoms,
R₃ is a hydrogen-atom or a radical with from 1 to 10 carbon atoms, and
X is a hydrogen atom, an alkyl group, an aryl group, an alkoxy group or a vinyl group.

The present invention thus relates to a method of preparing a compound of formula (IV) by a reaction of catalytic hydrogenation of a compound of formula (III) notably comprising at least the following steps:

a) a step of pretreatment of the Raney catalyst with at least one buffer compound for maintaining a pH between 6 and 8 during the hydrogenation reaction of step b); and
b) a step of hydrogenation of a compound of formula (III) to form a compound of formula (IV); the pH of the reaction mixture now being between 6 and 8 during the hydrogenation reaction; and
c) optionally a step of isolation of the compound of formula (IV).

The present invention relates more particularly to a method of preparing 2-methylpentane-2-4-diol (HGL) by a reaction of catalytic hydrogenation of diacetone-alcohol (DAA), characterized in that the reaction is catalysed by a Raney catalyst pretreated with a buffer compound enabling said reaction to be maintained at a pH between 6 and 8 inclusive.

The present invention also relates to a compound of formula (IV) that can be obtained by the aforementioned method.

The radical can have from 1 to 10 carbon atoms and can be linear or branched, saturated or unsaturated, cyclic or non-cyclic, aromatic or non-aromatic. The radical can be a hydrocarbon radical. The radical can comprise heteroatoms, such as O, F and/or N. We may mention for example the following radicals: methyl, ethyl, propyl, phenyl, trifluoromethyl, methoxy, and ethoxy.

It is possible for example to use, as alkyl group, notably for the definition of radical X, a methyl, isobutyl, and ethyl.

It is possible for example to use, as aryl group, notably for the definition of radical X, a phenyl, methylphenyl, and hydroxyphenyl radical.

It is possible for example to use, as alkoxy group, notably for the definition of radical X, a methoxy, ethoxy, and isobutoxy radical.

It is possible for example to use a vinyl group for the definition of radical X.

As explained above, the compound of formula (III) is a β hydroxy carbonylated compound possessing an alcohol function on the β carbon of the carbonyl function, such as an aldehyde, ketone or ester function. As preferred β hydroxy carbonylated compound of the present invention, we may mention the following compounds: diacetone-alcohol (DAA), hydroxy-3 propanal, hydroxy-3 butanal, keto-3 hydroxy-5 methyl-5 heptane, hydroxy-3 ethyl-2 hexanal, and hydroxy-3 dihydrocinnamic aldehyde.

The compounds of formula (III) are notably obtained by a reaction of base catalysed aldolization between a compound of formula (I) $(R^1)(R^2)C=O$ with a compound of formula (II) $R^3$—$CH_2$—COX. The compound of formula (II) can be an ester, a ketone, or an aldehyde; i.e. an enolizable compound, possessing at least one hydrogen atom on the α carbon of the CO, in the reaction of base catalysed aldolization.

We may mention for example as compound of formula (IV), the following compounds: methyl-2 pentanediol-2,4 (HGL), propanediol-1,3, butanediol-1,3, ethyl-2 hexanediol-1,3, methyl-5 heptanediol-3,5, and phenyl-1 propanediol-1,3.

The present invention therefore consists of treating the catalyst by bringing it in contact with a buffer compound, before carrying out the hydrogenation reaction. In the sense of the invention, buffer means a compound capable of approximately maintaining a pH between 6 and 8 during the hydrogenation reaction.

The reaction of hydrogenation of the β hydroxy carbonylated compounds is in itself well known by a person skilled in the art.

The reaction of the invention can be carried out continuously or discontinuously. The reaction can be carried out at a temperature between 70 and 150° C. The reaction can be carried out at a pressure between 5 and 50 bar, notably between 10 and 25 bar. The reaction time, for synthesizing an optimum amount of the compound of formula (IV), can be between 5 minutes and 5 hours.

The hydrogenation reaction is notably carried out in the liquid phase. The hydrogen can notably be dissolved wholly or partly in the compound of formula (III).

The reaction can notably be carried out in a continuous reactor, perfectly stirred for the liquid phase. The gas can be introduced either by systems of plunger tubes or by means of an auto-suction turbine or any other means, for example with an external recirculating loop. It is also possible to use a continuous reactor of the piston type such as a bubble column or a reactor with venturi ejector.

Generally from 0.1 to 20 wt. % of catalyst is used, relative to the weight of the compound of formula (III).

Generally from 0.01 to 2 wt. % of buffer compound is used, relative to the weight of the compound of formula (III). Generally from 0.1 to 20 wt. % of buffer compound is used, relative to the weight of the catalyst.

The Raney catalyst according to the invention can be a Raney nickel, a Raney cobalt or a Raney copper. These porous catalysts are well known and are generally called skeletal catalysts or sponge catalysts. Raney nickel is a solid catalyst used in numerous industrial processes. It is notably used as a heterogeneous catalyst for a great variety of reactions in organic chemistry, most often for hydrogenation reactions. Raney nickel is made by treating a powder of nickel-aluminium alloy with concentrated soda. In the course of this treatment, called "activation", most of the aluminium of the alloy is dissolved, with parallel evolution of much hydrogen. The resultant porous structure has a very high specific surface of 100 m²/g, which contributes to its efficiency as a catalyst.

There are numerous buffers, used alone or in combination, for approximately maintaining a pH between 6 and 8 during the reaction of hydrogenation of the compound of formula (III) according to the present invention. Buffer compound means, according to the invention, a solution containing an acid and its conjugated base, which has the property of not allowing its pH to change significantly despite addition of a base or of an acid to the medium. The solution generally has an acid/base concentration ratio between 0.01 and 100. We may notably mention organic or inorganic buffer compounds mentioned in the following documents: Good, N. E., et al. (1966) Hydrogen Ion Buffers for Biological Research. Biochemistry 5(2), 467-477; CRC Handbook of Chemistry and Physics, CRC Press Inc. David R. Lide, 1992-1993, 73rd edition, pages 8-37-8-42.

The buffer compound according to the invention can be selected from the group consisting of:
monobasic potassium phosphate,
monobasic sodium phosphate,
monobasic lithium phosphate,
2-[(2-hydroxy-1,1-bis(hydroxymethypethyl)amino] ethanesulphonic acid
sodium salt of N-[tris(hydroxymethyl)methyl]-2-aminoethanesulphonic acid
1,4-piperazinediethanesulphonic acid
sodium salt of 1,4-piperazinediethanesulphonic acid
sesquisodium salt of 1,4-piperazinediethanesulphonic acid
disodium salt of 1,4-piperazinediethanesulphonic acid
dipotassium salt of 1,4-piperazinediethanesulphonic acid
3-(N-morpholino)propanesulphonic acid
β-hydroxy-4-morpholinepropanesulphonic acid
sodium salt of 3-(N-morpholinyl)-2-hydroxypropanesulphonic acid
3-(N-morpholino)propanesulphonic acid
sodium salt of 3-(N-morpholino)propanesulphonic acid
hemisodium salt of 3-(N-morpholino)propanesulphonic acid
4-(N-morpholino)butanesulphonic acid
potassium salt of N-(2-hydroxyethyl)piperazine-N'-(2-ethanesulphonic) acid
hemisodium salt of 4-(2-hydroxyethyl)piperazine-1-ethanesulphonic acid
3-(N,N-bis[2-hydroxyethyl]amino)-2-hydroxypropanesulphonic acid
2,2-bis(hydroxymethyl)-2,2',2''-nitrilo-triethanol
1,3-bis[tris(hydroxymethyl)methylamino]propane
2,2-bis(hydroxymethyl)-2,2',2''-nitrilo-triethanol
N,N-bis(2-hydroxyethyl)-2-aminoethanesulphonic acid
sodium salt of N,N-bis(2-hydroxyethyl)-2-aminoethanesulphonic acid
N-(2-acetamido)iminodiacetic acid
monosodium salt of N-(2-acetamido)iminodiacetic acid
N-(2-acetamido)-2-aminoethanesulphonic acid
dibasic sodium citrate It should be noted that one or more buffer agents can be used during the reaction.

The pretreatment can be carried out by mixing the catalyst with the buffer compound for a time generally between 1 hour and 24 hours. Mixing can be carried out without particular stirring and at room temperature. The buffer can be in liquid form and the catalyst can be in the form of powder.

The catalyst thus pretreated is then brought in contact with the reaction mixture of the present invention.

At the end of the hydrogenation reaction, a mixture is discharged comprising the compound of formula (III), the compound of formula (IV), the catalyst and some by-products. The catalyst can be separated from the organic products by any means of solid/liquid separation, for example a filter or a decanter. The liquid obtained can notably be sent to a distillation column for separating the compound of formula (III) and the compound of formula (IV).

Special terminology is used in the description so as to facilitate understanding of the principle of the invention.

However, it must be understood that no limitation of the scope of the invention is intended by the use of this special terminology. Modifications, enhancements and improvements can notably be envisaged by a person skilled in the art on the basis of his own general knowledge.

The term and/or includes the meanings and, or, as well as all other possible combinations of the elements associated with this term.

Other details or advantages of the invention will become clearer from the examples given hereunder solely as a guide.

EXPERIMENTAL SECTION

Example 1

An autoclave reactor with a capacity of 150 ml is charged with DAA (80 g), Raney nickel (8 g) and optionally variable amounts of buffer. The Raney nickel catalyst can be washed with distilled water for a week to lower the basicity of the catalyst. This is the procedure used conventionally for Raney nickel catalysts in the reaction of hydrogenation of DAA. The catalyst can also be pretreated beforehand by mixing it with $KH_2PO_4$ for some hours.

The autoclave is sealed, and then purged with nitrogen and with hydrogen. The autoclave is then placed under hydrogen pressure at 20 bar and heated to a temperature of 100° C. Magnetic stirring is carried out at 1500 revolutions per minute. The data of the reaction, such as temperature, pressure, hydrogen consumption, reaction time and conversion are measured or calculated throughout the reaction. At the end of the reaction, the reactor is cooled and a sample is measured by gas chromatography and characterized using a mass spectrometer.

The selectivity S of a chemical reaction specifies the amount of desired product formed relative to the number of moles of the limiting reactant consumed. It indicates whether several reactions take place in parallel, leading to unwanted by-products, or whether the required reaction is the only one consuming the reactant.

The results are presented in the following Table 1:

TABLE 1

| Tests | Catalyst | Buffer | Conversion (%) | Selectivity (%) |
|---|---|---|---|---|
| C1 | Washed | — | 98.29 | 96.48 |
| C2 | Not washed | Acetic acid (pH 7.0) | 99.96 | 40.89 |
| C3 | Not washed | $KH_2PO_4$ 5% | 99.99 | 43.52 |
| 1 | Not washed | Pretreatment $KH_2PO_4$ 5% | 99.99 | 98.41 |
| 2 | Washed | Pretreatment $KH_2PO_4$ 5% | 99.97 | 98.42 |

The percentage of $KH_2PO_4$ is expressed by weight relative to the weight of the catalyst.

In test C1, the catalyst was washed with distilled water for 7 days. It is observed that the selectivity is inadequate, owing to formation of IPA. In test C2, the catalyst was not washed with water beforehand but was pretreated with an aqueous solution containing acetic acid to obtain a pH of 7. The selectivity observed is very poor owing to massive formation of IPA. In test C3, the catalyst was neither washed nor pretreated. Only $KH_2PO_4$ was added to the reaction mixture. Very poor selectivity is still observed.

In test 1, the unwashed catalyst was pretreated with $KH_2PO_4$. Very good selectivity is observed. In test 2, the catalyst was washed and pretreated. An equivalent selectivity was observed. It thus appears that pretreatment of the catalyst with a buffer according to the present invention makes it possible not only to obtain excellent selectivity, but also to eliminate a step of preliminary washing of the catalyst.

Example 2

The reaction is carried out in the same way as in example 1 but in the presence of 0.5 wt. % of Raney nickel relative to the weight of DAA.

The results are presented in the following Table 2:

TABLE 2

| Tests | Catalyst | Buffer | Conversion (%) | Selectivity (%) |
|---|---|---|---|---|
| C4 | Washed | — | 95.56 | 93.58 |
| 3 | Washed | Pretreatment $KH_2PO_4$ 5% | 95.17 | 96.34 |
| 4 | Washed | Pretreatment $KH_2PO_4$ 5% | 84.70 | 96.54 |

The percentage of $KH_2PO_4$ is expressed by weight relative to the weight of the catalyst.

We thus observe very good selectivity even in the presence of a small amount of catalyst; whereas the use of a large amount of catalyst, of the order of 5-20% relative to the DAA to be hydrogenated, is known from the prior art.

The invention claimed is:

1. A method of preparing a compound of formula (IV) by a reaction of catalytic hydrogenation of a compound of formula (III), said compound of formula (III) being obtained by a reaction of base catalysed aldolization, wherein said hydrogenation reaction is catalyzed by a Raney catalyst that was pretreated with at least one buffer compound enabling said hydrogenation reaction to be maintained at a pH between 6 and 8;

the compounds of formula (III) and (IV) are as follows:

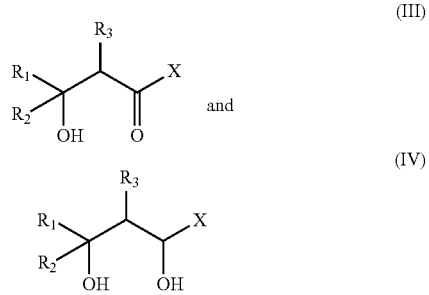

in which:
  $R^1$ is a radical with from 1 to 10 carbon atoms,
  $R^2$ is a hydrogen atom or a radical with from 1 to 10 carbon atoms,
  $R^3$ is a hydrogen atom or a radical with from 1 to 10 carbon atoms, and
  X is a hydrogen atom, an alkyl group, an aryl group, an alkoxy group, or a vinyl group.

2. The method of preparing a compound of formula (IV) by a reaction of catalytic hydrogenation of a compound of formula (III) according to claim 1, comprising at least the following steps:
  a) a step of pretreating the Raney catalyst with at least one buffer compound for maintaining a pH between 6 and 8 during the hydrogenation reaction of step b);

b) a step of hydrogenating a compound of formula (III) to form a compound of formula (IV); the pH of the reaction mixture now being between 6 and 8 during the hydrogenation reaction; and c) a step of isolating the compound of formula (IV).

3. The method according to claim 1, wherein the radical is selected from the group consisting of methyl, ethyl, propyl, phenyl, trifluoromethyl, methoxy, and ethoxy.

4. The method according to claim 1, wherein the alkyl group is selected from the group consisting of methyl, isobutyl, and ethyl.

5. The method according to claim 1, wherein the aryl group is selected from the group consisting of methylphenyl, and hydroxyphenyl.

6. The method according to claim 1, wherein the alkoxy group is selected from the group consisting of methoxy, ethoxy, and isobutoxy.

7. The method according to claim 1, wherein the compound of formula (III) is selected from the group consisting of diacetone-alcohol (DAA), hydroxy-3 propanal, hydroxy-3 butanal, keto-3 hydroxy-5 methyl-5 heptane, hydroxy-3 ethyl-2 hexanal, and hydroxy-3 dihydrocinnamic aldehyde.

8. The method according to claim 1, wherein the compound of formula (IV) is selected from the group consisting of: methyl-2 pentanediol-2,4 (HGL), propanediol-1,3, butanediol-1,3, ethyl-2 hexanediol-1,3, methyl-5 heptanediol-3,5, and phenyl-1 propanediol-1,3.

9. The method according to claim 1, wherein the hydrogenation reaction is carried out in the liquid phase; the hydrogen being dissolved wholly or partly in the compound of formula (III).

10. The method according to claim 1, wherein from 0.1 to 20 wt. % of catalyst is used relative to the weight of the compound of formula (III).

11. The method according to claim 1, wherein from 0.01 to 2 wt. % of buffer compound is used relative to the weight of the compound of formula (III).

12. The method according to claim 1, wherein from 0.1 to 20 wt. % of buffer compound is used relative to the weight of the catalyst.

13. The method according to claim 1, wherein the Raney catalyst is a Raney nickel, a Raney cobalt or a Raney copper.

14. The method according to claim 1, wherein the buffer compound is selected from the group consisting of:
monobasic potassium phosphate,
monobasic sodium phosphate,
monobasic lithium phosphate,
2-[(2-hydroxy-1,1-bis(hydroxymethyl)ethyl)amino]ethanesulphonic acid
sodium salt of N-[tris(hydroxymethyl)methyl]-2-aminoethanesulphonic acid
1,4-piperazinediethanesulphonic acid
sodium salt of 1,4-piperazinediethanesulphonic acid
sesquisodium salt of 1,4-piperazinediethanesulphonic acid
disodium salt of 1,4-piperazinediethanesulphonic acid
dipotassium salt of 1,4-piperazinediethanesulphonic acid
3-(N-morpholino)propanesulphonic acid
β-hydroxy-4-morpholinepropanesulphonic acid
sodium salt of 3-(N-morpholinyl)-2-hydroxypropanesulphonic acid
3-(N-morpholino)propanesulphonic acid
sodium salt of 3-(N-morpholino)propanesulphonic acid
hemisodium salt of 3-(N-morpholino)propanesulphonic acid
4-(N-morpholino)butanesulphonic acid
potassium salt of N-(2-hydroxyethyl)piperazine-N'-(2-ethanesulphonic) acid
hemisodium salt of 4-(2-hydroxyethyl)piperazine-1-ethanesulphonic acid
3-(N,N-bis[2-hydroxyethyl]amino)-2-hydroxypropanesulphonic acid
2,2-bis(hydroxymethyl)-2,2',2''-nitrilo-triethanol
1,3-bis[tris(hydroxymethyl)methylamino]propane
2,2-bis(hydroxymethyl)-2,2',2''-nitrilo-triethanol
N,N-bis(2-hydroxyethyl)-2-aminoethanesulphonic acid 1 sodium salt of N,N-bis(2-hydroxyethyl)-2-aminoethanesulphonic acid
N-(2-acetamido)iminodiacetic acid
monosodium salt of N-(2-acetamido)iminodiacetic acid
N-(2-acetamido)-2-aminoethanesulphonic acid
dibasic sodium citrate.

15. The method according to claim 1, wherein X is a vinyl group.

* * * * *